(12) United States Patent
Chen

(10) Patent No.: US 6,689,894 B1
(45) Date of Patent: Feb. 10, 2004

(54) PROCESS FOR PREPARING FATTY ACID ZINC SALTS

(75) Inventor: Bing-Lin Chen, Germantown, TN (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/358,654

(22) Filed: Feb. 5, 2003

(51) Int. Cl.[7] .............................................. C07C 51/00
(52) U.S. Cl. ..................................................... 554/156
(58) Field of Search ......................................... 559/156

(56) References Cited

U.S. PATENT DOCUMENTS

| | | | |
|---|---|---|---|
| 3,476,786 A | 11/1969 | Lally et al. | 260/413 |
| 3,803,188 A | 4/1974 | Scott et al. | 260/413 |
| 4,060,535 A | 11/1977 | Cinco | 260/414 |
| 4,294,771 A | 10/1981 | Pietralla et al. | 260/413 |
| 4,307,027 A | 12/1981 | Borzelli et al. | 260/413 |
| 4,316,852 A | 2/1982 | Blachford | 260/414 |
| 4,473,504 A | 9/1984 | Odashima et al. | 260/414 |
| 5,164,523 A | 11/1992 | Hudson et al. | 554/75 |

*Primary Examiner*—Deborah D. Carr
(74) *Attorney, Agent, or Firm*—Michael P. Dilworth

(57) ABSTRACT

A process for preparing fatty acid zinc salts comprising the steps of:

stirring a slurry mixture comprising zinc oxide, at least one catalyst, and water at a temperature in the range of from about 55° C. to about 65° C.; adding at least one fatty acid in its liquid state to said stirred slurry mixture; and reacting the fatty acid with the zinc oxide in the presence of the catalyst in the water at a temperature of from about 60° C. to about 75° C. until substantially all of the fatty acid has reacted. The final product mixture can then be filtered and dried to give a fatty acid zinc salt in high yield.

16 Claims, No Drawings

PROCESS FOR PREPARING FATTY ACID ZINC SALTS

BACKGROUND OF THE INVENTION

1. Field of the Invention

The present invention relates to a process for preparing fatty acid zinc salts in high yield by reaction of zinc oxide, fatty acids, and a catalyst, preferably in the presence of a surfactant, in water at a relatively low reaction temperature.

2. Description of Related Art

Metal soaps, such as zinc soaps (i.e., fatty acid zinc salts), have been used as anti-blocking and anti-caking agents, lubricant and mold release agents, thickening agents, waterproofing agents, and the like. They generally possess many of the desirable properties of the fatty acids from which zinc salts are manufactured.

Various processes, including precipitation and fusion processes, to produce metal soaps for industrial uses are known in the art.

U.S. Pat. No. 3,803,188 discloses that metallic soaps of Group II of the Periodic Table can be prepared by dispersing a metal oxide in a higher fatty acid and mixing therewith 3.5 to 40 mole equivalents of water based on the fatty acid. Surfactants are said to be useful catalysts for the reaction.

Precipitation processes produce metallic soaps by reaction of an aqueous solution of a water-soluble metal salt and a fatty acid alkali metal salt, whereupon the metal soap precipitates out of the solution. These precipitation processes are expensive owing to the large amount of water-soluble inorganic salt by-produced causing water pollution problems, and the requirement of time consuming filtering, washing, and drying steps to isolate a purified metal soap from the aqueous product mixture.

In fusion processes, metal soaps are produced by reaction of a metal oxide, hydroxide, carbonate, or acetate with a molten fatty acid at a high temperature. These fusion processes have disadvantages that limit their use. For example, most commercial fusion processes use expensive high temperature equipment and complex handling procedures, and need long reaction times for a complete reaction. They usually yield large lumps of discolored metal soaps that must be ground to a desired particle size, often causing serious air pollution problems.

U.S. Pat. No. 4,307,027 discloses metallic salts of higher molecular weight fatty acids that are produced in a continuous process by feeding fatty acid and base into a plug flow reactor to maintain a residence time of about 2 to about 60 minutes at a temperature of about 75° F. to about 280° F. to obtain a metallic salt, then grinding the metallic salt in a hammer mill to obtain coarse particles and then grinding the coarse particles in a jet mill to obtain fine particles of the metallic salt. Optionally, the fatty acid and base may be fed initially into a stirred-tank reactor to maintain a residence time of about 10 to about 80 minutes at a temperature of from about 115° F. to about 300° F. to initiate metallic salt reaction before feeding the metallic salt reaction mixture into the plug flow reactor.

U.S. Pat. No. 4,316,852 discloses metallic soaps, particularly zinc soaps that are produced from a reaction mixture initially comprising a metal oxide or hydroxide, for example, zinc oxide, water and a glyceryl ester, particularly a triglyceride, the ester and said metal oxide or hydroxide being present in at least approximately stoichiometric amounts. The reaction mixture is agitated and the reactants are reacted in the agitated mixture to produce a metallic soap and glycerine, at a temperature at which the metallic soap is molten, in the presence of an excess of water effective to dissolve the glycerine formed in the reaction mixture such that reaction between by-product glycerine and the product metallic soap is substantially hindered. Eventually, the reaction mixture is allowed to separate into an aqueous layer and a molten layer of product metallic soap under a pressure such that the aqueous layer is essentially quiescent, and the molten metallic soap layer is dissociated from the aqueous layer. In this way, it is said, metallic soaps of high purity can be obtained.

U.S. Pat. No. 5,164,523 describes a fusion process for the rapid production of a granular metal soap that passes a mixture of metal (e.g., zinc) oxide, one or more molten fatty acids and a catalyst through a heated reactor to form molten metallic soap which is then ejected through a spray nozzle in a cooling tower to form a granular soap product. Use of a spiral tubular reactor with a rapid heating coil is disclosed. The reaction is conducted under pressure to maintain water generated by the reaction in the liquid state. Flashing of the reaction water in the cooling tower aids in cooling and formation of fine granules.

Other processes for preparing metal soaps are known wherein a mixture containing a metal oxide, hydroxide, or carbonate, an organic acid or fatty acid, optionally in the presence of a catalyst, such as water, is subjected to vigorous agitation or grinding at a temperature below the melting point of the organic acid and the metal soap. The products prepared in this manner after drying are light-colored, finely divided powders. However, the metal soap formation reaction often takes place slowly in these processes resulting in products having high levels of unreacted organic acid or fatty acid.

U.S. Pat. No. 3,476,786 discloses that finely divided water insoluble metallic salts of higher fatty acids can be produced by grinding solid fatty acids with particular solid metals, metal oxides, metal hydroxides, metal carbonates or mixtures thereof in the presence of a catalyst and in the absence of water.

U.S. Pat. No. 4,060,535 discloses that metal salts of organic acids can be produced rapidly and efficiently by subjecting a reaction mixture that contains a metal oxide, hydroxide, or carbonate, an organic acid that has a melting point above 20° C., and a small amount of water to vigorous agitation in an apparatus having attrition and shearing action at a temperature that is below the melting point of the organic acid and below the melting point of the metal salt that is being produced until substantially all of the organic acid has reacted.

U.S. Pat. No. 4,294,771 discloses a method for producing metal soaps by reacting aliphatic carboxylic acids with metal oxides, metal hydroxides and/or metal carbonates, wherein the metal soaps are directly obtained in the form of granulates without requiring an additional granulating step.

U.S. Pat. No. 4,473,504 discloses a method of producing large granules of metallic soap by reacting a water-insoluble metal carbonate and fatty acid.

It is an object of the present invention to provide a low temperature process for producing good quality fatty acid zinc salts in high yield.

SUMMARY OF THE INVENTION

In accordance with the present invention, there is provided a low temperature process for rapidly and efficiently preparing fatty acid zinc salts. The process comprises adding a fatty acid in its liquid state to an aqueous slurry of zinc oxide and a catalyst, preferably in the presence of a surfactant, and reacting the mixture at a temperature of from about 60° C. to about 75° C. for about 5 to about 120 minutes or until substantially all of the fatty acid has reacted.

The catalyst is present in the reaction mixture at a level from about 0.01 weight percent to about 0.2 weight percent. Fatty acids that can be employed in the practice of this invention include monocarboxylic acids having from about 8 to about 30 carbon atoms. The surfactant is used at an amount of about 0.05% to about 2% by weight of the whole reaction mixture. An advantage of the present invention is that fatty acid zinc salts having good quality and physical forms suitable for direct use are produced rapidly and economically.

More particularly, the present invention is directed to a process for preparing fatty acid zinc salts comprising the steps of:

stirring a slurry mixture comprising zinc oxide, at least one catalyst, and water at a temperature in the range of from about 55° C. to about 65° C.;

adding at least one fatty acid in its liquid state to said stirred slurry mixture; and reacting the fatty acid with the zinc oxide in the presence of the catalyst in the water at a temperature of from about 60° C. to about 75° C. until substantially all of the fatty acid has reacted.

Preferably, the product mixture is then cooled to a temperature in the range of from about 25 to about 30° C., filtered, and dried to provide a quantitative yield of fatty acid zinc salt having good color and a free fatty acid content of less than 1% by weight.

DESCRIPTION OF THE PREFERRED EMBODIMENTS

In accordance with the present invention, a fatty acid, such as commercial fatty acid (e.g., Industrene 7018 from Crompton Corp., titer=58–62° C.), is melted, if necessary, into a liquid state and held at about 75° C. The liquid fatty acid is added to a slurry of zinc oxide, a catalyst, such as citric or phosphoric acid, a surfactant, and water at about 55° C. The reaction mixture is stirred at a temperature of from about 60° C. to about 75° C. for about 5 to about 120 minutes or until substantially all of the fatty acid has reacted. The reaction is monitored by infrared spectrum and free fatty acid analyses. The aqueous product slurry mixture is then filtered and dried to yield a good quality fatty acid zinc salt powder that can be used directly without further processing steps.

Fatty acids used in the process of this invention include higher monocarboxylic acids preferably having from about 8 to about 30 carbon atoms, more preferably from about 12 to about 22 carbon atoms. These acids can be saturated or unsaturated, substituted or unsubstituted. A single fatty acid or a combination of various fatty acids may be used. For example, any of capric acid, lauric acid, myristic acid, palmitic acid, stearic acid, oleic acid, linoleic acid, linolenic acid, arachidic acid, behenic acid, erucic acid, and the like, either alone, in combination with each other, or with any of the other fatty acids may be used. The fatty acid may have hydroxyl, carbonyl, or epoxy groups in the molecule including, for example, ricinoleic acid or 12-hydroxystearic acid. Commercially available fatty acids, such as stearic acid, palmitic acid, lauric acid, and commercially available blends of fatty acids also are useful in this process. Commercial stearic acid, which generally comprises about 50% to about 75% by weight of stearic acid, about 25% to about 50% by weight of palmitic acid, and small amounts of other $C_{12}$–$C_{22}$ fatty acids are especially useful and are preferred. For example, both Hystrene 7018 and Industrene 7018 from Crompton Corp. are commercial stearic acid having about 65–70% by weight of stearic acid, about 28% by weight of palmitic acid, and 2–5% by weight of other fatty acids. The fatty acid used in this process, if not liquid at room temperature, is initially heated to melt and kept in the molten state at a temperature of from about 70° to 75° C. before being used in later steps.

A zinc oxide:fatty acid mole ratio of about 1:2 is desirably used in the practice of this invention. More preferably, zinc oxide is introduced in an amount of about 0.50 to about 0.65 mole per mole of the fatty acid used.

Water is preferably used as a reaction medium and is usually employed in the range of from about one to about three times the weight of the resulting fatty acid zinc salt.

A catalyst is used in the present process to induce the reaction between the zinc oxide and the fatty acid at a lower temperature and to promote the reaction to a greater degree of completion than would otherwise be possible. Preferably, the catalyst makes possible a reaction temperature for the zinc oxide/fatty acid reaction of from about 60° C. to about 75° C. to give a quantitative yield of fatty acid zinc salt. Preferred catalysts for use in the practice of this invention include citric acid (anhydrous, ACS reagent) and phosphoric acid (85% solution in water, ACS reagent). An amount of catalyst capable of lowering the reaction temperature to the desired range while achieving a quantitative yield of the product is sufficient. Preferably, the catalyst is used in an amount of from about 0.01 to about 0.50%, more preferably in an amount of from about 0.05 to about 0.20%, by weight of the whole reaction mixture.

Although the process of this invention can be carried out in the absence of surfactant, surfactant is desirably introduced to keep the fatty acid zinc salt dispersed evenly in the product slurry mixture, which is beneficial to the final product particle sizes. The surfactant is preferably used in an amount of from about 0.05 to about 2%, more preferably from about 0.1 to about 0.5%, by weight of the reaction mixture.

The surfactant(s) used may be anionic, cationic, or nonionic. Nonionic surfactants useful in this invention include cellulose ethers, such as hydroxypropyl methylcellulose (Methocel F50 from Dow); ethoxylated primary or secondary alcohols, such as Tergitol 15-S-7 from Dow, Witconol SN-50 from Crompton Corp., Ethosperse LA-4 from Lonza Co., and Iconol TDA-6 from BASF; ethoxylated alkly phenols, such as Witconol NP-100 from Crompton Corp. and Makon 10 from Stepan Co; and ethoxylated fatty acids, such as Ninex MT-610 from Stepan Co. The degree of ethoxylation in the nonionic surfactants is generally from about 2 to about 12 ethylene oxide units. Anionic surfactants, such as sodium alkylbenzene sulfonates (e.g. Witconate 90), ethoxylated alkylphenol sulfates and sulfonates, alcohol sulfates, alcohol phosphates, sulfosuccinates, and the like, can be used.

In a preferred embodiment of this invention, zinc oxide and a catalyst are first dispersed in water containing a surfactant to form a zinc oxide slurry. The slurry is heated to and maintained at a temperature that is higher than the melting point of the fatty acid used. A fatty acid in its liquid state is then added gradually to the zinc oxide slurry with effective stirring. The reaction of the fatty acid with the zinc oxide is monitored by the infrared spectrum and free fatty acid analyses of the reaction mixture. A complete reaction of fatty acid with zinc oxide is indicated by the disappearance of infrared absorption of the reaction mixture at about 1723.4 cm$^{-1}$, characteristic of fatty acid, and the appearance of the characteristic absorption at about 1550 cm$^{-1}$ of fatty acid zinc salt. The complete reaction is also evidenced when little or no free fatty acid (e.g., less than 1% by weight) is present in the product. When the reaction has been completed, the product slurry is filtered and dried to afford the fatty acid zinc salt powder in quantitative yield. The fatty acid zinc salts prepared in this way show good color and contain less than 1% by weight of free fatty acid. Generally, fatty acid zinc salts containing less than 1% by weight of unreacted free fatty acid are considered acceptable by industry standards.

The advantages and the important features of the present invention will be more apparent from the following examples.

EXAMPLE 1

(Comparative Example)

Zinc oxide (6.6 grams), Tergitol 15-S-7 (2 grams), and water (70 grams) were placed in a beaker and heated to 55° C. with stirring to form a slurry mixture. Stearic acid (43 grams of Industrene 7018, titer=58–62° C.) was heated to about 75° C. and the resulting molten stearic acid was added gradually to the slurry mixture. The reaction mixture was stirred at 60–65° C. for three hours. A sample was drawn from the reaction mixture, dried, and analyzed by infrared spectrum to show about a 10% yield of zinc stearate.

EXAMPLE 2

(Comparative Example)

A molten stearic acid (22 grams, Industrene 7018) was added gradually to a stirred slurry comprising zinc oxide (3.6 grams), Methocel F50 (0.2 gram), Tergitol 15-S-7 (0.2 gram), and water (70 grams) at 55° C. The mixture was stirred at 65–70° C. for 1 hour to produce a yield of zinc stearate of about 50% by its infrared spectrum.

EXAMPLE 3

A molten stearic acid (22.2 grams, Industrene 7018) was added gradually to a stirred slurry mixture of zinc oxide (4 grams), citric acid (0.1 gram), and water (70 grams) at 60° C. The mixture was stirred at 60–70° C. for 30 minutes to afford a product mixture with zinc stearate floating, which was filtered and dried to give a quantitative yield of zinc stearate as shown by its infrared spectrum.

EXAMPLE 4

A molten stearic acid (22.2 grams, Industrene 7018) was gradually added to a stirred slurry mixture of zinc oxide (4 grams), citric acid (0.1 gram), Methocel F50 (0.2 gram), Tergitol 15-S-7 (0.2 gram), and water (70 grams) at 55° C. The mixture was stirred at 60–70° C. for 30 minutes to afford a product mixture that showed the yield of zinc stearate to be about 100% by its infrared spectrum.

EXAMPLE 5

A molten stearic acid (23 grams, Industrene 7018) was added gradually to a stirred slurry of zinc oxide (3.9 grams), citric acid (0.08 gram), Methocel F50 (0.1 gram), Tergitol 15-S-7 (0.3 gram), and water (70 grams) at 60° C. The mixture was stirred at 65–70° C. for 15 minutes to give a reaction mixture showing the yield of zinc stearate to be about 100% by its infrared spectrum.

EXAMPLE 6

A quantity of 35 grams of Pamolyn 100, a high purity oleic acid containing about 90% oleic acid, was added gradually to a stirred slurry of zinc oxide (5.4 grams), citric acid (0.05 gram), Witconate 90 (1.18 grams), and water (60 grams) at 65° C. The mixture was stirred at 55–65° C. for 10 minutes to give a quantitative yield of zinc oleate as indicated by the infrared spectrum of the dried product.

EXAMPLE 7

A molten stearic acid (29.7 grams, Industrene 7018) was added gradually to a stirred slurry of zinc oxide (4.86 grams), phosphoric acid (0.13 gram, 85% solution in water), Tergitol 15-S-7 (0.8 gram), and water (65 grams) at 65° C. The mixture was stirred at 55–73° C. for one hour to give a quantitative yield of zinc stearate as shown by the infrared spectrum of the final product.

EXAMPLE 8

A molten stearic acid (202 grams of Hystrene 4516) was added gradually to a stirred slurry of zinc oxide (32 grams), citric acid (0.5 gram), Methocel F50 (3 grams), and water (560 grams) at 65° C. The mixture was stirred at 65–75° C. for 1 hour to afford after filtering and drying a 100% yield of zinc stearate as indicated by its infrared spectrum. The resulting product was a white powder having free fatty acid content of 0.22% by weight.

EXAMPLE 9

A molten stearic acid (29.5 grams, Hystrene 7018) was added gradually to a stirred mixture of zinc oxide (4.9 grams), citric acid (0.06 gram), Tergitol 15-S-7 (0.35 gram) and water (66 grams) at 65° C. The reaction mixture was stirred at 60–70° C. for one hour, cooled to 25° C., filtered and dried to give 32.6 grams (99.1% yield) of zinc stearate white powder that showed 0.08% water, 13.6% ash, 0.49% by weight of free fatty acid, and a melting point of 126° C.

EXAMPLE 10

A molten stearic acid (29.5 grams, Hystrene 7018) was added gradually to a stirred mixture of zinc oxide (4.9 grams), phosphoric acid (0.1 gram), Tergitol 15-S-7 (0.2 gram), and water (66 grams) at 65° C. The reaction mixture was stirred at 60–70° C. for one hour, cooled to 25° C., filtered, and dried to afford 32.4 grams (98.8% yield) of zinc stearate white powder having 0.1% water, 14.3% ash, 0.44% by weight of free fatty acid, and a melting point of 126° C.

In view of the many changes and modifications that can be made without departing from principles underlying the invention, reference should be made to the appended claims for an understanding of the scope of the protection to be afforded the invention.

What is claimed is:

1. A process for preparing fatty acid zinc salts comprising the steps of:

stirring a slurry mixture comprising zinc oxide, at least one catalyst, and water at a temperature in the range of from about 55° C. to about 65° C.;

adding at least one fatty acid in its liquid state to said stirred slurry mixture; and reacting the fatty acid with the zinc oxide in the presence of the catalyst in the water at a temperature of from about 60° C. to about 75° C. until substantially all of the fatty acid has reacted.

2. The process of claim 1 further comprising the steps of filtering and drying the product mixture.

3. The process of claim 2 further comprising the step of cooling the product mixture prior to the filtering and drying steps.

4. The process of claim 1 wherein the fatty acid is a monocarboxylic acid having from about 8 to about 30 carbon atoms.

5. The process of claim 1 wherein the catalyst is citric acid.

6. The process of claim 1 wherein the catalyst is phosphoric acid.

7. The process of claim 1 wherein the slurry mixture further comprises at least one surfactant.

8. The process of claim 7 wherein the surfactant is selected from the group consisting of cellulose ethers, ethoxylated alkyl alcohols, ethoxylated alkylphenols, and alkylbenzene sulfonates.

9. The process of claim 4 wherein the fatty acid is stearic acid.

10. The process of claim 4 wherein the fatty acid is a high purity oleic acid containing about 90% oleic acid.

11. The process of claim 1 wherein zinc oxide is used in an amount of from about 0.5 to about 0.65 mole per mole of fatty acid.

12. The process of claim 1 wherein the catalyst is used in an amount of from about 0.01 to about 0.50% by weight of the whole reaction mixture.

13. The process of claim 7 wherein the surfactant is used in an amount of from about 0.05 to about 2% by weight of the reaction mixture.

14. The process of claim 1 wherein water is used as a reaction medium in the range of from about 1 to about 3 times the weight of the resulting fatty acid zinc salt.

15. The process of claim 1 wherein the said reaction is continued for a period of from about 5 to about 120 minutes.

16. The process of claim 1 wherein the reaction is continued until the fatty acid zinc salt that is being produced has a free fatty acid content of less than 1.0% by weight.

* * * * *